US011701324B2

(12) United States Patent
Gerton et al.

(10) Patent No.: US 11,701,324 B2
(45) Date of Patent: Jul. 18, 2023

(54) VAGINAL HYDROGEL FOR DELIVERY OF THERAPEUTICS

(71) Applicants: Marina Lee Gerton, Salt Lake City, UT (US); Brenda K. Mann, Salt Lake City, UT (US)

(72) Inventors: Marina Lee Gerton, Salt Lake City, UT (US); Brenda K. Mann, Salt Lake City, UT (US)

( * ) Notice: Subject to any disclaimer, the term of this patent is extended or adjusted under 35 U.S.C. 154(b) by 44 days.

(21) Appl. No.: 17/179,854

(22) Filed: Feb. 19, 2021

(65) Prior Publication Data
US 2021/0169797 A1 Jun. 10, 2021

Related U.S. Application Data

(62) Division of application No. 16/233,102, filed on Dec. 27, 2018, now Pat. No. 10,959,945.

(60) Provisional application No. 62/645,801, filed on Mar. 21, 2018.

(51) Int. Cl.
| A61K 9/06 | (2006.01) |
| A61K 9/00 | (2006.01) |
| A61K 47/38 | (2006.01) |
| A61K 47/32 | (2006.01) |
| A61K 31/4164 | (2006.01) |
| A61K 9/70 | (2006.01) |
| A61K 47/10 | (2017.01) |
| A61P 15/02 | (2006.01) |

(52) U.S. Cl.
CPC ............. *A61K 9/06* (2013.01); *A61K 9/0034* (2013.01); *A61K 9/7015* (2013.01); *A61K 31/4164* (2013.01); *A61K 47/10* (2013.01); *A61K 47/32* (2013.01); *A61K 47/38* (2013.01); *A61P 15/02* (2018.01)

(58) Field of Classification Search
CPC ...... A61K 9/06; A61K 9/0034; A61K 9/7015; A61K 31/4164; A61K 47/10; A61K 47/32; A61K 47/38; A61P 15/02
USPC .......................................................... 514/54
See application file for complete search history.

(56) References Cited

U.S. PATENT DOCUMENTS

| 8,859,523 B2 | 10/2014 | Prestwich et al. |
| 2007/0134334 A1 | 6/2007 | Hahn et al. |
| 2014/0271491 A1 | 9/2014 | Gittard et al. |
| 2017/0224708 A1 | 8/2017 | Gravett et al. |
| 2019/0290582 A1 | 9/2019 | Gerton et al. |
| 2019/0365902 A1 | 12/2019 | Mann |

OTHER PUBLICATIONS

Valenta et al. The use of mucoadhesive polymers in vaginal delivery. Advanced Drug Delivery Reviews 57 (2005) 1692-1712. (Year: 2005).*
Almomen et al., Thermosensitive progesterone hydrogel: a safe and effective new formulation for vaginal application. Pharm Res. 2015; 32:2266-79.
Ibrahim et al., Development and characterization of thermosensitive pluronic-based metronidazole in situ gelling formulations for vaginal application. Acta Pharm. 2012; 62:59-70.
Kawarkhe et al., Designing of the mucoadhesive intravaginal spermicidal films. Indian J Pharm Sci. 2010; 72:652-5.
De Araujo Pereira et al., Vaginal mucoadhesive drug delivery systems. Drug Devel Ind Pharm. 2012; 38:643-52.
Chen et al, Evaluation of the efficacy and safety of hyaluronic acid vaginal gel to ease vaginal dryness: A multicenter, Yandomized, controlled, open-label, parallel-group, clinical trial. J Sex Med. 2013; 10:1575-84.
Hiorth et al., Bioadhesive mini-tablets for vaginal drug delivery. Pharmaceutics. 2014; 6:494-511.
Nowak et al., Preactivated hyaluronic acid: A potential mucoadhesive polymer for vaginal delivery. Intl J Pharm. 2015; 478:383-9.
Liu et al., Biocompatibility and stability of disulfide-crosslinked hyaluronan films. Biomaterials. 2005; 26:4737-46.
Nair et al., The thiol-Michael addition click reaction: A powerful and widely used tool in materials chemistry. Chem Mater. 2014; 26:724-44.
Vanderhooft et al., Synthesis and characterization of novel thiol-reactive poly(ethylene glycol) cross-linkers for extracellular-matrix-mimetic biomaterials. Biomacromolecules. 2007; 8:2883-9.
Mather et al., Michael addition reactions in macromolecular design for emerging technologies. Progress in Polymer Science. 2006; 31:487-531.
Niu et al., Thiol/Acrylate-modified PEO-PPO-PEO triblocks used as reactive and thermosensitive copolymers. Biomacromolecules 2008; 9:2621-2628.
Valenta et al., The use of mucoadhesive polymers in vaginal delivery. Advanced Drug Discovery Reviews 2005 57:1692-1712.
Non-final Office Action dated May 7, 2020 for U.S. Appl. No. 15/991,870.
Final Office Action dated Nov. 9, 2020 for U.S. Appl. No. 15/991,870.
Non-final Office Action dated Apr. 22, 2020 for U.S. Appl. No. 16/233,102.
Final Office Action dated Aug. 11, 2020 for U.S. Appl. No. 16/233,102.
Notice of Allowance dated Nov. 20, 2020 for U.S. Appl. No. 16/233,102.

(Continued)

*Primary Examiner* — Yih-Horng Shiao
(74) *Attorney, Agent, or Firm* — Laurence & Phillips IP Law

(57) ABSTRACT

The composition is a hydrogel which may be used to deliver therapeutics vaginally. The hydrogel may include a glycosaminoglycan. The glycosaminoglycan may include multiple thiol groups. The composition may also include a molecule that includes at least two thiol reactive sites. The composition may include a mucoadhesive agent as well as a therapeutic agent. The composition may deliver the therapeutic at a pH that is optimal for the vaginal environment, namely between about 3.5 and 5.0.

20 Claims, 5 Drawing Sheets

(56) References Cited

OTHER PUBLICATIONS

Corrected Notice of Allowance dated Feb. 2, 2021 for U.S. Appl. No. 16/233,102.
Notice of Allowance dated Nov. 2, 2021 for U.S. Appl. No. 15/991,870.
Response to non-final Office Action dated Jun. 30, 2021 for U.S. Appl. No. 15/991,870.
Response to Final Office Action dated Feb. 8, 2021 for U.S. Appl. No. 15/991,870.
Response to non-final Office Action dated Aug. 6, 2020 for U.S. Appl. No. 15/991,870.
Response After Final Office Action dated Oct. 28, 2020 for U.S. Appl. No. 16/233,102.
Non-final Office Action dated Mar. 31, 2021 for U.S. Appl. No. 15/991,870.
U.S. Appl. No. 17/590,213, Office Action dated Mar. 2, 2023.

* cited by examiner

Cumulative drug release over 144 hours from the films containing 20 mg/mL metronidazole (M) or metronidazole benzoate (MB). MC: methylcellulose; 100%: 5 mg/ml; 150%: 7.5 mg/ml. Assuming drug was evenly dispersed throughout the films, each 6 mm diameter disc should have contained 1.13 mg. n=5; error bars=SD Swelling of metronidazole and metronidazole benzoate films after rehydrating in SVF for 24 hours. n=3; error bars=SD.

Stress vs strain curve for films containing 5 mg/ml methylcellulose during tensile testing. Control films contain no drug; MB = metronidazole benzoate.

Stress vs strain curve for films containing 7.5 mg/ml methylcellulose during tensile testing. Control films contain no drug; MB = metronidazole benzoate.

VAGINAL HYDROGEL FOR DELIVERY OF THERAPEUTICS

RELATED APPLICATIONS

This application is a continuation application of U.S. patent application Ser. No. 16/233,102, filed Dec. 27, 2018, which claims the benefit of U.S. Provisional Patent Application No. 62/645,801, filed Mar. 21, 2018, each of which is hereby incorporated by reference in its entirety.

TECHNICAL FIELD

This disclosure relates to compounds and methods of drug delivery, in particular, delivery of gynecological therapeutic compounds.

BACKGROUND

Bacterial Vaginosis:

Vaginitis affects millions of women around the world every year, and bacterial vaginosis is the most common form. Currently, marketed treatments are either intravaginal creams and gels or systemic oral treatments, and the most common drugs are metronidazole, clindamycin, and tinidazole. Metronidazole is the most common drug due to the high efficacy of treating harmful bacteria, along with the lack of effect on beneficial lactobacilli. Some of the problems, however, with current treatments include the messiness of intravaginal gels and creams, the potentially lowered efficacy of the drugs in gels and creams as the drug is lost through vaginal secretions, pH imbalances with products that do not have pHs of 3.5-5, and for systemic treatments, the problem of introducing the drugs to the entire body, which can produce side effects. Therefore, a better method for effectively delivering metronidazole or other therapeutics to the vagina over multiple days, at a proper pH for the vaginal environment, and with high drug efficacy is needed.

Hydrogels and Films:

Hydrogels have been utilized as a biomaterial in a variety of medical applications owing to their high water content, similarity in physical properties to many tissues, and potential for incorporating drugs. These applications include wound healing, tissue engineering and regenerative medicine, drug delivery, and joint lubrication. These hydrogels can be based on natural or synthetic materials, or a combination of the two. Typically, hydrogels will be crosslinked, either through physical interaction—such as simple entanglement, hydrogen bonding, or ionic interaction—or through covalent bonds. Either method of forming hydrogels is typically done at or near what is considered standard physiological pH (i.e., pH 7.4). However, many environments in the body are at a lower pH. In particular, the average pH of the vagina is typically between about 3.2 and 5.0, an environment that favors microflora that are beneficial to the vagina. If the pH of the vagina is increased, a shift in the balance of the microflora occurs, allowing for infection and eventually leading to vaginosis or vaginitis.

Currently available treatments often treat either the infection or the inflammation, but not both. Additionally, many of these treatments are provided in either a liquid or hydrogel format, but not at a pH that is beneficial for the vaginal environment. As indicated above, a film format may be easier to use and provide better drug delivery and efficacy.

Thus, there is a need for a film formed from a hydrogel that can be delivered vaginally and that is at a pH targeted for this environment, namely between about 3.5 and 5.0, and which may be used for delivery of therapeutics.

BRIEF SUMMARY OF THE DISCLOSURE

We disclose a composition which may be used to deliver a therapeutic agent vaginally. The composition may include one or more glycosaminoglycans. Each of the one or more glycosaminoglycans may include a plurality of thiol groups. The composition may also include a molecule that includes at least two thiol-reactive sites. In an example, the molecule may be poly(ethylene glycol) diacrylate or poly(ethylene glycol) bisbromoacetate. The thiol-reactive sites may be chosen from a list that includes, but is not limited to, acrylate, methacrylate, bromoacetate, iodoacetate, bromoacetamide, iodoacetamide, or maleimide. The composition may also include a mucoadhesive agent. In an example, the mucoadhesive agent may be methylcellulose, hydroxymethylcellulose, hydroxyethylcellulose, or hydroxypropylcellulose. The composition may be provided in a dried form and have a pH of between about 3.2 and about 5.0 when hydrated. A therapeutic agent may be included in the composition.

In some embodiments, the one or more glycosaminoglycan comprises a modified hyaluronic acid. In an example, the modified hyaluronic acid is a thiol-modified hyaluronic acid. In an example, the thiol-modified hyaluronic acid may be crosslinked to a poly(ethylene glycol) which includes a plurality of thiol-reactive sites.

In some embodiments, the therapeutic agent which may be included in the composition may include one or more of the agents in the following list: an antimicrobial agent, an antibacterial agent, an antiviral agent, an estrogen, and an estrogen derivative.

In some embodiments, the therapeutic agent may have a solubility in water of less than about 1.0 mg/ml. In some embodiments, the therapeutic agent may have a concentration in the composition which is at least about 10 times greater than the solubility of the therapeutic agent in water. In some embodiments, the concentration of the therapeutic agent is at least about 100 times greater than the solubility of the therapeutic agent in water.

We also disclose a method for making a drug delivery composition including the step of forming a mixture of glycosaminoglycan that has multiple thiol groups, a molecule that includes at least two thiol-reactive sites, a mucoadhesive agent, a therapeutic agent, and a buffer which has a pH between about 3.2 and about 5.0. The glycosaminoglycan and the molecule may be allowed to covalently crosslink; and the mixture allowed to dry.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings.

DETAILED DESCRIPTION OF THE DISCLOSURE

Definitions

Figure 1:
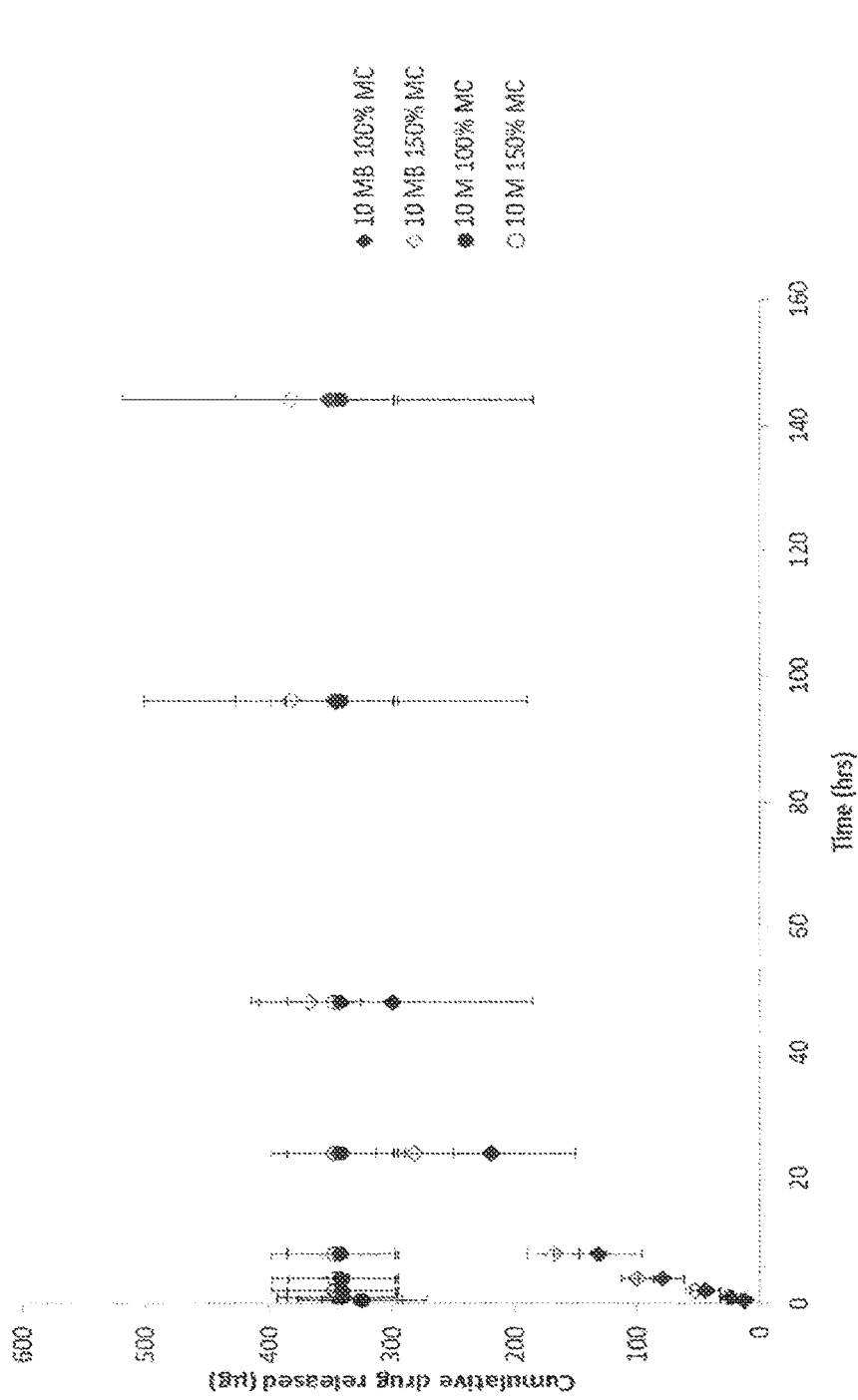
FIG. 1 is a graph which illustrates the cumulative drug release over 144 hours from the films containing 10 mg/ml metronidazole (M) or metronidazole benzoate (MB).

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

Covalent crosslinking of the hydrogels described herein, and the films formed from them, may be achieved through means including, but not limited to, disulfide crosslinking, Michael-type addition, or photopolymerization. The hydrogel may be based on an anionic polysaccharide, which may be naturally anionic (for example, hyaluronic acid or alginate), or may be modified to introduce or increase negative charge, for example, through substitution of hydroxyl groups with carboxyl groups. Particularly suitable are glycosaminoglycans, and a modified hyaluronic acid (HA). HA is a natural anionic polysaccharide that is found throughout the body and has been shown to have anti-inflammatory properties. Additionally, HA provides moisturization and lubrication.

The hyaluronic acid may be modified to have a higher number of negative charges (e.g., carboxymethyl hyaluronic acid) for ionic crosslinking, and/or to include groups capable of covalent crosslinking, for example, thiol or amine groups, thiol-reactive or amine-reactive groups, or photopolymerizable groups. These photopolymerizable groups may include methacrylate, acrylate, or vinyl groups. The chemical structure of hyaluronic acid, along with modifications mentioned above, is shown below. The R groups indicated are modifications made to introduce groups for altering material properties or for crosslinking. In the case of a thiol-modified HA, the hydrogel may be formed by disulfide crosslinking or by combining with a molecule having thiol-reactive groups.

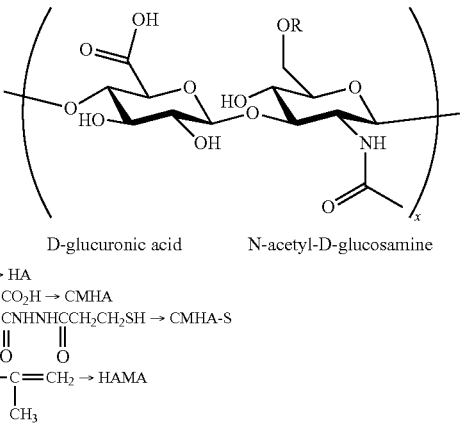

D-glucuronic acid     N-acetyl-D-glucosamine

R = H → HA
 = CH$_2$CO$_2$H → CMHA
 = CH$_2$CNHNHCCH$_2$CH$_2$SH → CMHA-S
 = C—C=CH$_2$ → HAMA

One common crosslinker is poly(ethylene glycol) (PEG), which can be modified to have reactive endgroups, for example, bromoacetate or acrylate groups, added to aid in crosslinking. The chemical structure of poly(ethylene glycol) is shown below. The R groups indicated are modifications made to introduce reactive endgroups for crosslinking. Although the addition of both bromoacetate or acrylate groups are examples of Michael-type addition, the crosslinking reaction of a thiol with bromoacetate occurs faster than a thiol with acrylate. Other thiol-reactive endgroups could also be used to crosslink a thiolated polysaccharide. Alternatively, PEG with photopolymerizable endgroups could be used in conjunction with a hyaluronic acid or other polysaccharide having photopolymerizable endgroups, allowing for altering of material properties for the resultant photocrosslinked hydrogel.

Thiol groups on the anionic polysaccharide are useful, as thiol groups may be beneficial for interacting with the vaginal mucosa, allowing the hydrogel film to remain in the vagina for an extended period of time. For example, when the hydrogel composition has a thiolated polysaccharide and is combined with a thiol-reactive molecule, the ratio of thiol groups to thiol-reactive groups may be about 2:1 or greater. This can allow for some thiols to be used for covalent crosslinking, while having thiol groups remaining that may be used to interact with the vaginal mucosa.

The hydrogels may be formed at a pH between about 3.5 and 5.0, utilizing an appropriate buffer, for example, a lactic acid or citric acid buffer. A lactic acid buffer may be particularly appropriate for the vaginal environment, as lactic acid/lactate is produced naturally in the vagina. Crosslinking via Michael-type addition is typically done at a pH of about 6.5-8.5, as the crosslinking proceeds extremely slowly outside of this range. However, to ensure proper hydrogel formation at lower pH, such as between 3.5 and 5.0, the crosslinking mixture may be placed in a sealed, humidified environment for several days until the hydrogel has formed. Additionally, the temperature of the humidified environment may be increased slightly during this time (to ~35-40° C.) to facilitate crosslinking without degrading the polysaccharide.

The crosslinking solution may be placed in a mold in which the hydrogel will take the shape of the mold, but the hydrogel and/or resultant film does not adhere to the mold and is therefore easily released. Once the hydrogel has formed, a film may be formed from the hydrogel by either allowing the hydrogel to air dry, or by freezing and lyophilizing the hydrogel. Air drying will result in a film that is much thinner than the original hydrogel, whereas lyophilization will result in a film with a spongier texture that has a shape very similar to the original hydrogel. The dried film or sponge may then be ground into a powder, if desired.

The resultant hydrogel may be more or less tightly crosslinked by varying the degree of covalent crosslinking in the hydrogel. This may be accomplished by changing the concentration of the polysaccharide, an additional crosslinking molecule, or the number of reactive groups on the polysaccharide or additional crosslinking molecule.

One or more therapeutic agents may be incorporated within the gel, and may be incorporated by mixing, covalently attaching the therapeutic agent to a component of the gel, or through ionic interaction with a component of the gel. The one or more therapeutic agents may include antimicrobials, for example, antibiotics and antivirals, hormones, for example, estrogen or an estrogen derivative, steroids, and anti-inflammatories. A therapeutic agent with a lower solubility in water will release more slowly from the gel, leading to extended delivery of the therapeutic. The therapeutic agent can be incorporated within the gel at concentrations higher than the solubility of the therapeutic agent in water, although the insoluble amount will appear as small particles within the hydrogel and resultant dried material. In an example, the therapeutic agent may have a solubility in water of less than about 1.0 mg/ml. In an example, the therapeutic agent may have a concentration in the composition at least about 10 times greater than the solubility of the therapeutic agent in water. In an example, the therapeutic agent may have a concentration in the composition at least about 100 times greater than the solubility of the therapeutic agent in water.

Other components may also be incorporated into the hydrogel to aid in flexibility of the resultant films, enhance mucoadhesion to tissue, or both. Mucoadhesive agents include cellulose derivatives, for example, methylcellulose, hydroxymethylcellulose, hydroxyethylcellulose, and hydroxypropylcellulose. The cellulose derivatives may also improve flexibility of the hydrogel films.

EXAMPLES

Materials

Thiol-Crosslinked Films:

Thiolated carboxymethyl HA (CMHA-S; 10 mg/mL), poly(ethylene glycol)-diacrylate (PEGda, MW=3350; 5.86 mg/mL), poly(ethylene glycol)-bisbromoacetate (PEGbba, MW=3350; 5.86 mg/mL), methylcellulose (MC; 5 or 7.5 mg/mL).

Drugs:

metronidazole (5-37.5 mg/mL), metronidazole benzoate (5-37.5 mg/mL).

Lactic Acid Buffer:

30.36 mM sodium lactate, 22 mM lactic acid, 8 mg/mL sodium chloride, in DI $H_2O$, pH 4-5.

Simulated Vaginal Fluid (SVF):

sodium chloride (3.51 g/L), calcium hydroxide (222 mg/L), urea (400 mg/L), glucose (5.00 g/L), bovine serum albumin (18 mg/L), potassium hydroxide (24.96 µl/L), glycerol (126.88 µl/L), acetic acid (0.954 ml/L), lactic acid (1.958 ml/L).

Phosphate Buffered Saline (PBS):

sodium chloride (8 g/L), potassium chloride (0.2 g/L), sodium phosphate (1.44 g/L), potassium phosphate (0.24 g/L), in DI $H_2O$, pH 7.4.

Photo-Crosslinked Films:

methacrylated HA (HAMA; 10 mg/mL), PEGda (25 mg/mL), 2,2-dimethoxy-2-phenyl acetophenone (DMPA) or Irgacure 2959 (10 µl/mL), methylcellulose (5 mg/mL).

Molds Used to Create Hydrogels:

polyvinyl chloride (PVC), polycarbonate base with silicone sides, silicone.

Example 1—Creating Thiol-Crosslinked Films

CMHA-S was dissolved in lactic acid buffer; methylcellulose and drug were then added to the CMHA-S solution. PEGbba was separately dissolved in lactic acid buffer. The CMHA-S solution and PEGbba solution were then combined and mixed by inversion or drawing up and down a pipette. The final mixture had concentrations of CMHA-S, PEGbba, MC, and drug as indicated above under "Materials". The final mixture was then transferred to a mold. The mold was placed in a container along with open dishes of water to provide humidity, and a lid placed on the container to seal the container, preventing water from evaporating from the mixture during crosslinking and formation of the hydrogel. A small portion of the final mixture was also placed in a sealed tube to monitor crosslinking. When crosslinking was complete, the lid was removed from the container and the hydrogel was allowed to air dry, forming a thin film.

For this combination of CMHA-S and PEGbba in lactic acid buffer having a pH of 4.5, the mixture crosslinked and formed a solid hydrogel in approximately 72 hours. Insoluble drug that had been incorporated within the mixture could be seen as small particles dispersed within the hydrogel and in the resultant thin film.

Example 2—Drug Release from Thiol-Crosslinked Films

Five 6 mm-diameter discs were punched out from each film formulation listed in Table 1. Each disc was placed in 1 ml of SVF in a microcentrifuge tube; the tubes were then placed in an incubator shaker at 37° C. The SVF release medium was removed and replaced with fresh SVF at 0.5, 1, 2, 4, 8, 24, 48, 96, and 144 hours. Aliquots of the SVF release medium from each sample at each time point were placed in a plate reader and the absorbance at 318 nm was determined. A standard curve of the drug (metronidazole or metronidazole benzoate) in SVF was used to calculate the concentration of drug in each sample of SVF release medium.

TABLE 1

Formulations of thiol-crosslinked films used in testing. All formulations had 10 mg/ml CMHA-S and 5.86 mg/ml PEGbba. Films were created according to the method in Example 1, utilizing silicone molds.

| Form-ulation # | Drug | Drug concentration (mg/ml) | Methylcellulose concentration (mg/ml) |
|---|---|---|---|
| 1 | Metronidazole benzoate | 10 | 5 |
| 2 | Metronidazole benzoate | 20 | 5 |
| 3 | Metronidazole benzoate | 10 | 7.5 |
| 4 | Metronidazole benzoate | 20 | 7.5 |
| 5 | Metronidazole | 10 | 5 |
| 6 | Metronidazole | 20 | 5 |
| 7 | Metronidazole | 10 | 7.5 |
| 8 | Metronidazole | 20 | 7.5 |

Figure 2:
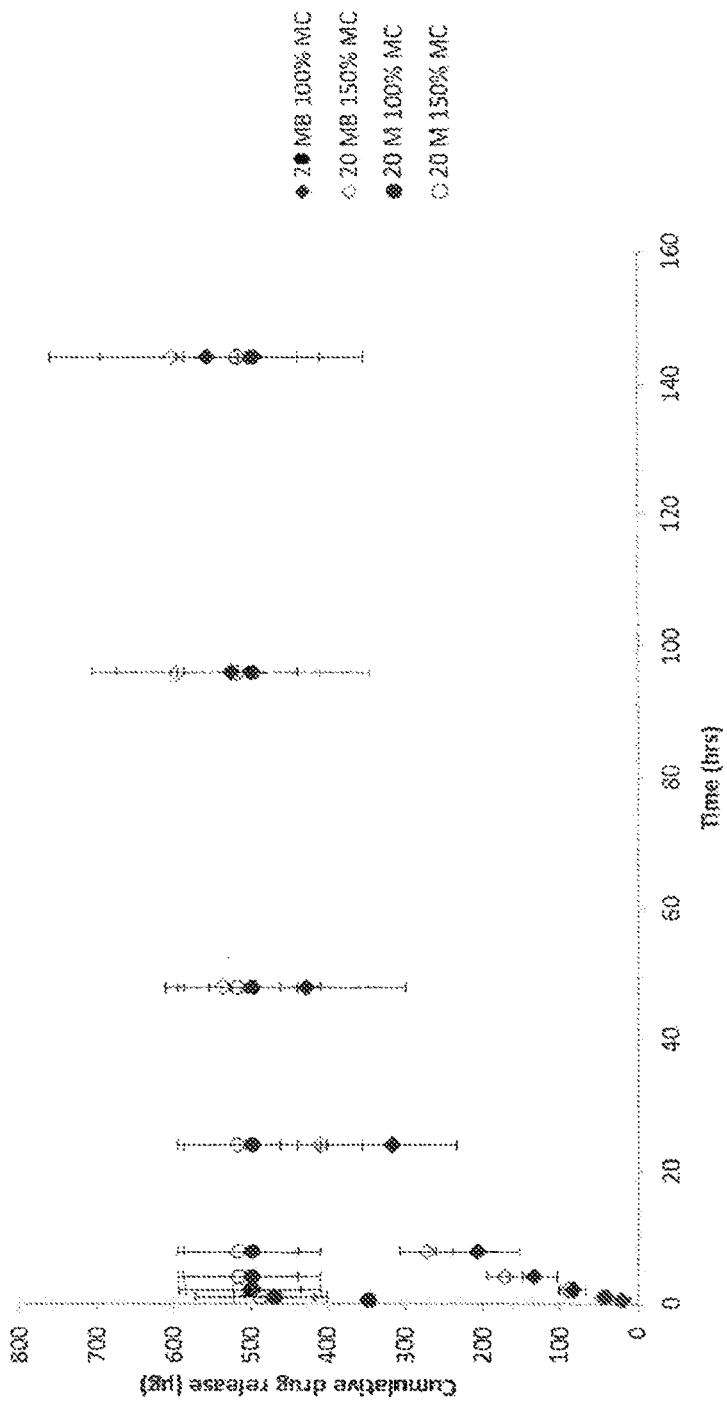
FIG. 2 is a graph which illustrates the cumulative drug release over 144 hours from the films containing 20 mg/ml metronidazole (M) or metronidazole benzoate (MB).

Release of metronidazole and metronidazole benzoate from thiol-crosslinked films is shown in FIGS. 1 and 2. More specifically, FIG. 1 is a graph which illustrates the cumulative drug release over 144 hours from the films containing 10 mg/mL metronidazole (M) or metronidazole benzoate (MB) while FIG. 2 is a graph which illustrates the cumulative drug release over 144 hours from the films containing 20 mg/mL metronidazole (M) or metronidazole benzoate (MB). While the metronidazole benzoate films released drug steadily over time, the metronidazole films dumped most of the released drug within an hour, which is likely due to the solubility differences between the drugs (solubility in water: 10 mg/ml vs 0.1 mg/ml for metronidazole and metronidazole benzoate, respectively). The metronidazole benzoate films also released more total drug than did the metronidazole films. The concentration of MC also seemed to have an effect on the release of the drug, particularly for the metronidazole benzoate films. The films with the higher MC concentration released more drug over time than the films with lower MC concentration; thus, MC may aid in drug release. Both of the metronidazole benzoate films with high MC concentration were also the ones to release the highest percentage of drug, relative to the predicted amount in each disc.

Example 3—Material Properties of Thiol-Crosslinked Films

Film Flexibility:

A qualitative assessment of film flexibility was performed by twisting, folding, and crumpling of the films. The metronidazole films were very brittle and had very little give. They could not be stretched at all, which was one characteristic property of the films without drug; nor could they be twisted. They would immediately break upon any twisting, and the films could not even reach a 90° twist. Additionally, they could be loosely folded, but not creased without breaking, and could therefore not be crumpled. The metronidazole benzoate films, on the other hand, could be folded, creased, and crumpled without any damage to the films. They could also be twisted at least 180° before any tearing occurred. The difference in flexibility between the metronidazole and metronidazole benzoate films is likely due to the higher concentration of actual dissolved drug in the metronidazole films, which more directly affects the film properties. The high MC concentration also aided in flexibility, though less so for the metronidazole films.

Mucoadhesivity:

The mucoadhesivity of films containing metronidazole benzoate and films without drug was assessed using bovine vaginal tissue. A piece of vaginal tissue was affixed to a half-cylinder of PVC pipe using superglue, such that the mucosal lining was facing outward. The PVC pipe was propped at an approximate 60° angle to simulate use under gravity. A strip of the film was placed on the mucosal lining. A syringe filled with SVF was placed in a syringe pump, and tubing was attached to the syringe with the outlet of the tubing placed just above the film on the tissue. The syringe pump was run at 2 different rates—1 ml/min, to simulate a rush of vaginal fluid, for 3 minutes; and 1.4 µl/min, to simulate average normal vaginal secretion, for up to 24 hours. The film was monitored for any slippage of the film during fluid flow. The films swelled as they became rehydrated with SVF, and some buckling of the films was noted during rehydration. However, all films remained in contact with the tissue throughout the testing and did not have any slippage. Therefore, the films demonstrated mucoadhesive properties, and swelling of the films during rehydration did not interfere with the films' interaction with the tissue.

Figure 3:
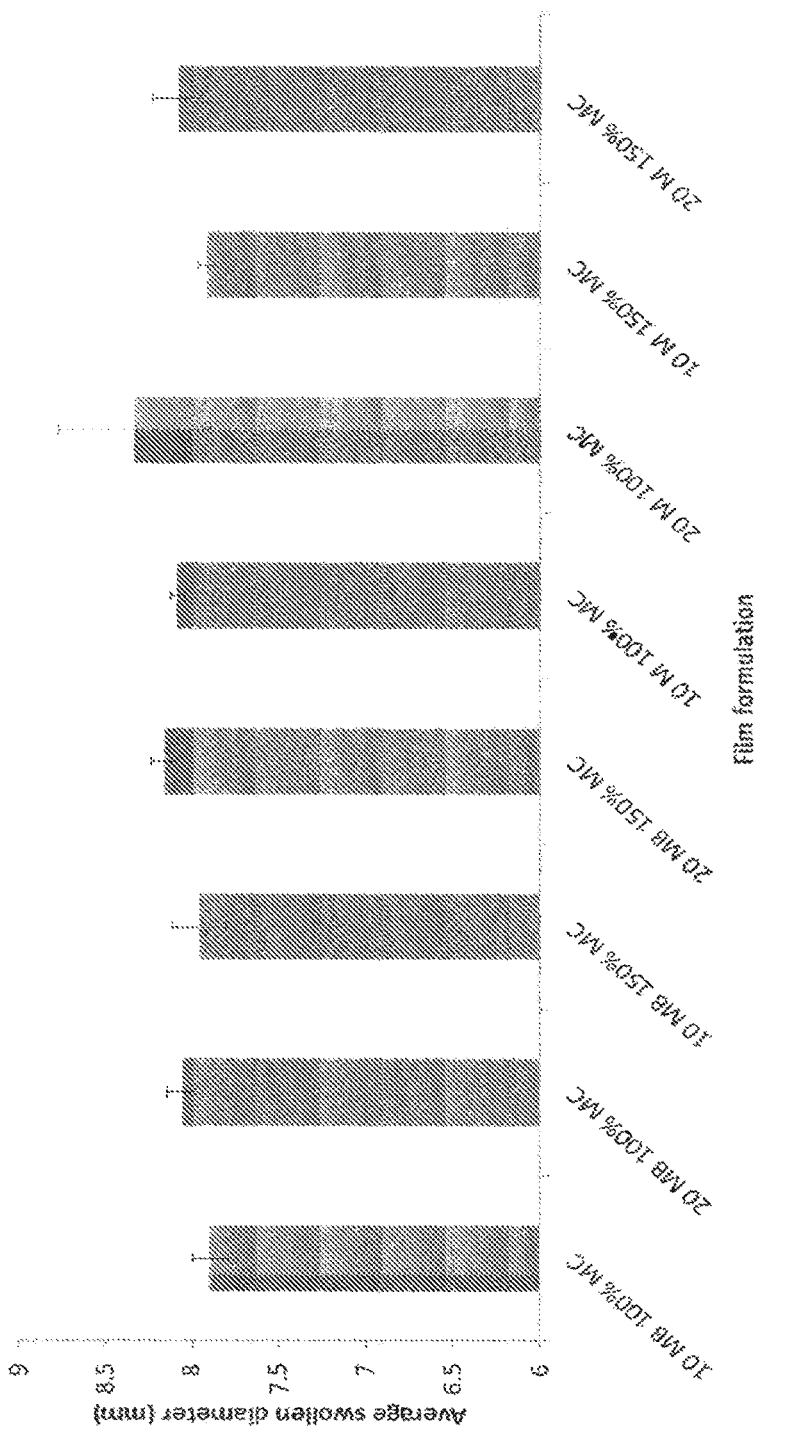
FIG. 3 is a bar graph which illustrates the swelling of metronidazole and metronidazole benzoate films after rehydrating in simulated vaginal fluid (SVF) for 24 hours.

Swelling:

To further assess swelling of the films when rehydrated, three 6 mm-diameter discs were punched out from each film formulation shown in Table 1. The discs were placed in a 24-well plate with 1 ml of SVF in each well. The film discs were allowed to rehydrate and swell in the SVF for 24 hours at 37° C. Images of the rehydrated discs were then taken using a stereomicroscope with camera attached, and diameters of the discs were determined using Image-J software. All of the film formulations swelled to about 8 mm in diameter as shown in FIG. 3. Although there was some slight variability with the different formulations, there was no significant difference in swelling when comparing the different film formulations. This swelling outward of the film is probably a rather beneficial property, as it provides more surface area for the film to interact with the mucosal lining.

Tensile Properties:

A dog-bone-shaped mold was used to cut five pieces of film from each metronidazole benzoate formulation and three pieces for each no drug formulation. The gage area of the cutouts measured 8 mm in length, 3 mm in width, and were approximately 0.1 mm and 0.25 mm in thickness for the films without and with drug, respectively. Each end of the film pieces was placed between the clamps of an Instron 5943. Tensile testing of the film pieces was performed, using a crosshead speed of 0.25 mm/min. Each trial was concluded when the film was fully torn across the gage area.

Figure 4:
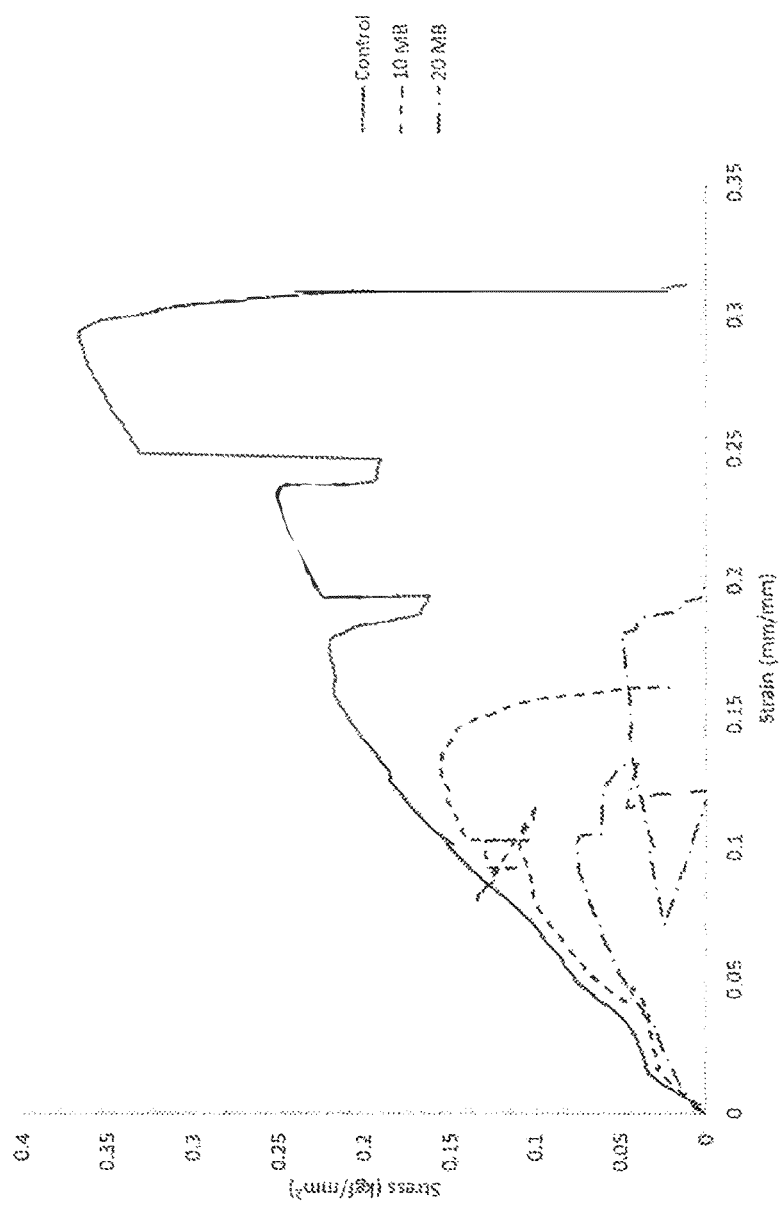
FIG. 4 is a graph which illustrates stress vs strain curve for films containing 5 mg/ml methylcellulose during tensile testing.
Figure 5:
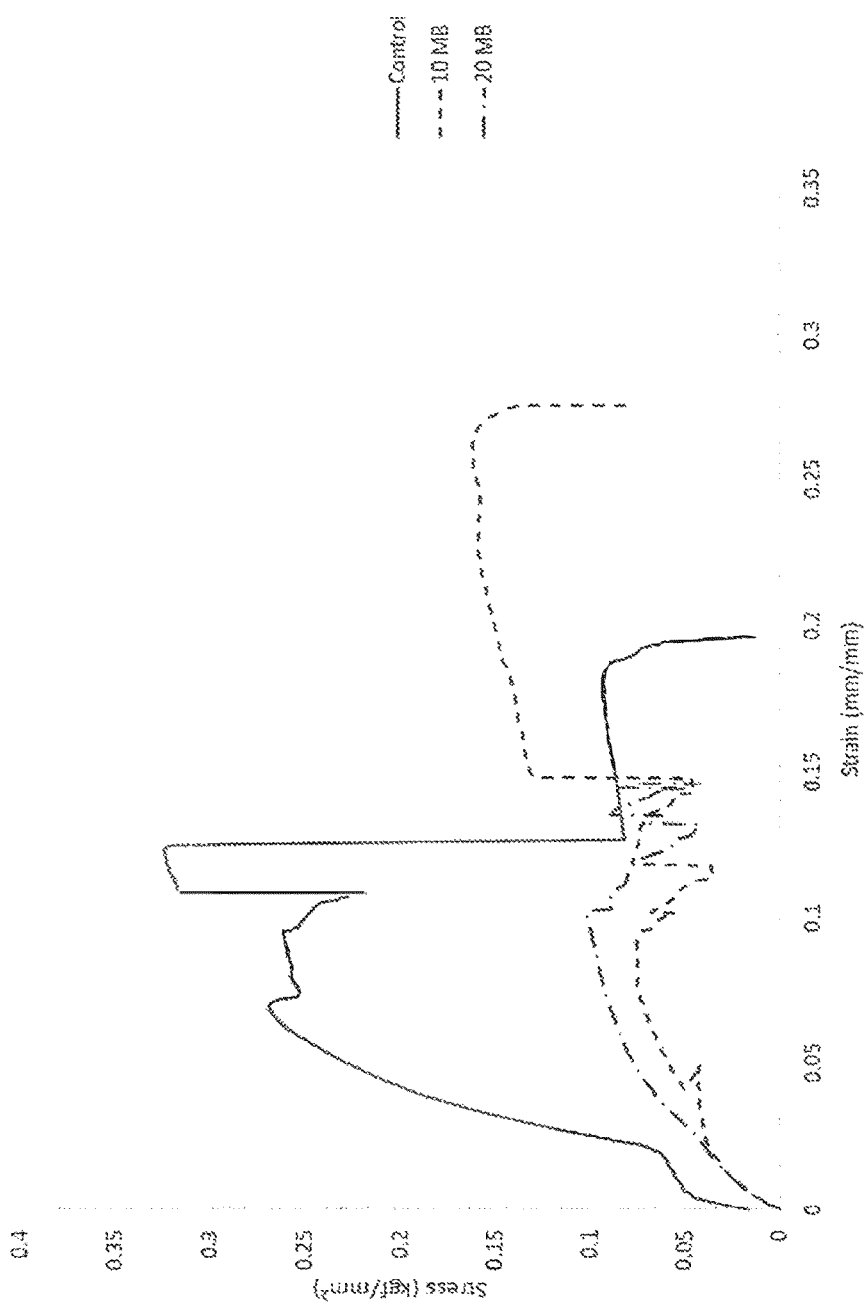
FIG. 5 is a graph which illustrates stress vs strain curves for films containing 7.5 mg/ml methylcellulose during tensile testing.

The results of the tensile strength tests were often highly variable as shown in FIGS. 4 and 5. Specifically, FIG. 4 illustrates the stress vs strain curve for films containing 5 mg/ml methylcellulose during tensile testing and FIG. 5 illustrates the stress vs strain curve for films containing 7.5 mg/ml methylcellulose during tensile testing. This variability may be due to the fact that the solutions used for the films are not homogeneous. In particular, the dispersal of the poorly soluble drug, and even the crosslinks between chains, are random and uneven. Therefore, each piece of film may behave differently from another piece of film, even from the same solution, and any visibly undetectable breaks along the edge of the gage area may create a false fail location. Therefore, hundreds of trials with each formulation may be necessary to acquire statistically significant data. Alternatively, a method of rendering the films more homogeneous may be useful.

Two of the measures that may be important for assessing film properties from this testing are the ultimate tensile strength (maximum stress achieved for the material during testing) and the strain at breakage. Regardless of the concentration of methylcellulose, an increased amount of drug in the film resulted in a significant decrease in the ultimate tensile strength. Further, the concentration of methylcellulose did not have a significant effect on the ultimate tensile strength, as the strength was similar when comparing formulations with the same amount of drug but different concentrations of methylcellulose. The strain at breakage, on the other hand, did not appear to be dependent on drug or methylcellulose concentration.

Example 4—Creating Photo-Crosslinked Films

HAMA was dissolved in lactic acid buffer; methylcellulose and drug were then added to the HAMA solution. PEGda was separately dissolved in lactic acid buffer. The HAMA solution and PEGda solution were then combined and mixed by inversion or drawing up and down a pipette. Photoinitiator, either DMPA or Irgacure, was then added and mixed by inversion. The final mixture had concentrations of HAMA, PEGda, MC, drug, and photoinitiator as indicated above under "Materials". The final mixture was then transferred to a mold. The mold was placed under a 365 nm-wavelength UV lamp for up to 10 minutes until the mixture was crosslinked, forming a hydrogel. The hydrogel was then allowed to air dry, forming a thin film.

Modifications and improvements of the embodiments specifically disclosed herein are within the scope of the following claims. Without further elaboration, it is believed that one skilled in the area can, using the preceding description, utilize the present disclosure to its fullest extent. Therefore, the Examples herein are to be construed as merely illustrative and not a limitation of the scope of the present invention in any way. The embodiments disclosed in which an exclusive property or privilege is claimed are defined as follows.

We claim:

1. A crosslinked composition comprising:
   a glycosaminoglycan comprising a plurality of thiol-reactive sites,
   a molecule A comprising at least two thiol groups,
   a mucoadhesive agent, and
   a therapeutic agent having a solubility in water of less than about 1.0 mg/mL,
   wherein the composition is dried by a process selected from air drying or lyophilization, and
   wherein the glycosaminoglycan is crosslinked to the molecule A at a pH selected from a value between about 3.2 and about 5.0.

2. The crosslinked composition of claim 1, wherein the glycosaminoglycan comprises a modified hyaluronic acid.

3. The crosslinked composition of claim 1, wherein the glycosaminoglycan comprises methacrylated or acrylated hyaluronic acid.

4. The crosslinked composition of claim 1, wherein the molecule A comprises a thiolated poly(ethylene glycol).

5. The crosslinked composition of claim 1, wherein the therapeutic agent has a concentration in the composition at least about 10 times greater than the solubility in water.

6. The crosslinked composition of claim 4, wherein the therapeutic agent has a concentration in the composition at least about 100 times greater than the solubility in water.

7. The crosslinked composition of claim 1, wherein the at least two thiol-reactive sites are independently selected from the group consisting of acrylate, methacrylate, bromoacetate, iodoacetate, bromoacetamide, iodoacetamide, and maleimide.

8. The crosslinked composition of claim 1, wherein the mucoadhesive agent is selected from the group consisting of methylcellulose, hydroxymethylcellulose, hydroxyethylcellulose, and hydroxypropylcellulose.

9. The crosslinked composition of claim 1, wherein the therapeutic agent comprises one or more of distinct agents in the following list: an antimicrobial agent, an antibacterial agent, an antiviral agent, an estrogen, and an estrogen derivative.

10. The crosslinked composition of claim 1, wherein the glycosaminoglycan is crosslinked to the molecule A at a pH consisting of a value between about 3.5 and about 4.5.

11. A method for making a crosslinked drug delivery composition comprising:
    forming a mixture comprising:
      a glycosaminoglycan comprising a plurality of thiol-reactive sites,
      a molecule A comprising at least two thiol groups,
      a mucoadhesive agent,
      a therapeutic agent having a solubility in water of less than about 1.0 mg/mL, and
      a buffer having a pH between about 3.2 and about 5.0;
    crosslinking the glycosaminoglycan and the molecule A at a pH selected from a value between about 3.2 and about 5.0; and
    drying the crosslinked mixture by a process selected from air drying or lyophilization.

12. The method of claim 11, wherein the glycosaminoglycan comprises a modified hyaluronic acid.

13. The method of claim 11, wherein the glycosaminoglycan comprises methacrylated or acrylated hyaluronic acid.

14. The method of claim 11, wherein the molecule A comprises a thiolated poly(ethylene glycol).

15. The method of claim 11, wherein the therapeutic agent is provided in the composition in a concentration of at least about 10 times greater than the solubility in water.

16. A crosslinked drug delivery composition made by the method of claim 11.

17. A crosslinked composition comprising:
    a modified hyaluronic acid comprising a plurality of thiol-reactive sites,
    poly(ethylene glycol) comprising at least two thiol groups, and
    a therapeutic agent,
    wherein the modified hyaluronic acid is crosslinked to the poly(ethylene glycol) at a pH selected from a value between about 3.2 and about 5.0, and the composition is dried by a process selected from air drying or lyophilization.

18. The crosslinked composition of claim 17, wherein the thiol-reactive sites are independently selected from the group consisting of acrylate, methacrylate, bromoacetate, iodoacetate, bromoacetamide, iodoacetamide, and maleimide.

19. The crosslinked composition of claim 17, wherein the therapeutic agent comprises one or more of distinct agents in the following list: an antimicrobial agent, an antibacterial agent, an antiviral agent, an estrogen, and an estrogen derivative.

20. The crosslinked composition of claim 17, wherein the therapeutic agent is provided in the composition in a concentration of at least about 10 times greater than the solubility in water.

* * * * *